US007741471B2

(12) United States Patent
Prudent et al.

(10) Patent No.: US 7,741,471 B2
(45) Date of Patent: Jun. 22, 2010

(54) REAGENTS FOR THE IMPROVED SYNTHESIS OF ISOGUANOSINE CONTAINING OLIGONUCLEOTIDES

(75) Inventors: James R. Prudent, Madison, WI (US); Christopher B. Sherrill, Madison, WI (US)

(73) Assignee: EraGen Biosciences, Inc., Madison, WI (US)

( * ) Notice: Subject to any disclaimer, the term of this patent is extended or adjusted under 35 U.S.C. 154(b) by 224 days.

(21) Appl. No.: 11/915,279

(22) PCT Filed: May 26, 2005

(86) PCT No.: PCT/US2005/018680

§ 371 (c)(1),
(2), (4) Date: Nov. 21, 2007

(87) PCT Pub. No.: WO2006/127009

PCT Pub. Date: Nov. 30, 2006

(65) Prior Publication Data

US 2008/0207890 A1    Aug. 28, 2008

(51) Int. Cl.
*C07H 21/00* (2006.01)
(52) U.S. Cl. ............... 536/25.3; 536/25.31; 536/25.32; 536/25.33; 536/25.34
(58) Field of Classification Search .................. None
See application file for complete search history.

(56) References Cited

U.S. PATENT DOCUMENTS

| 4,415,732 | A | 11/1983 | Caruthers et al. |
| 4,458,066 | A | 7/1984 | Caruthers et al. |
| 4,973,679 | A | 11/1990 | Caruthers et al. |
| 5,256,549 | A | 10/1993 | Urdea et al. |
| 5,430,138 | A | 7/1995 | Urdea et al. |
| 6,147,199 | A | 11/2000 | Seela et al. |
| 6,498,241 | B1 | 12/2002 | Seela et al. |

OTHER PUBLICATIONS

Roberts et al. Tetrahedron Letters (1995), vol. 36, pp. 3601-3604.*
Seela, Frank et al., "Oligonucleotides Containing Consecutive 2'-Deoxyisoguanosine Residues: Synthesis, Duplexes with Parallel Chain Orientation, and Aggregation," *Helvetica Chimica Acta*, 1997, vol. 80, pp. 73-85.

Seela, Frank et al., "Synthesis of Phosphonates and Oligodeoxyribonucleotides Derived from 2'-Deoxyisoguanosine and 2'-Deoxy-2-haloadenosines," *Helvetica Chimica Acta*, 1992, vol. 75, pp. 2298-2306.
Jurczyk, Simona C. et al., "Synthesis of Oligonucleotides Containing 2'-Deoxyisoguanosine and 2'-Deoxy-5-methylisocytidine Using Phosphoramidite Chemistry," *Helvetica Chimica Acta*, 1998, vol. 81, pp. 793-811.
Vu, Huynh et al., "Fast Oligonucleotide Deprotection Phosphoramidite Chemistry for DNA Synthesis," *Tetrahedron Letters*, 1990, vol. 31(50), pp. 7269-7272.
Roberts, Christopher et al., "Theoretical and Experimental Study of Isoguanine and Isocytosine: Base Pairing in an Expanded Genetic System," *J. Am. Chem. Soc.*, 1997, vol. 119, pp. 4640-4649.
Seela, Frank et al., "Quadruplex and Pentaplex Self-Assemblies of Oligonucleotides Containing Short Runs of 8-Aza-7-deaza-2'-deoxyisoguanosine or 2'-Deoxyisoguanosine," *Bioconjugate Chem.*, 2001, vol. 12, pp. 1043-1050.
McBride, Lincoln J. et al., "Amidine Protecting Groups for Oligonucleotide Synthesis," *J. Am. Chem. Soc.*, 1986, vol. 108, pp. 2040-2048.
Horn, Thomas et al., "Hybridization Properties of the 5-Methyl-Isocytidine/Isoguanosine Base Pair in Synthetic Oligodeoxynucleotides," *Tetrahedron Letters*, 1995, vol. 36(12), pp. 2033-2036.
Li, Hong et al., "Fluorescence quenching of parallel-stranded DNA bound ethidium bromide: the effect of 7-deaza-2'-deoxyisoguanosine and 7-halogenated derivatives," *Bioorganic & Medicinal Chemistry Letters*, 2004, vol. 24, pp. 6031-6034.
Seela, Frank et al., "Parallel-stranded oligonucleotide duplexes containing 5-methylisocytosine-guanine and isoguanine-cytosine base pairs," *Tetrahedron Letters*, 1999, vol. 55, pp. 9481-9500.
Rice, Kevin P. et al., "RecA Protein Promotes Strand Exchange with DNA Substrates Containing Isoguanine and 5-Methyl Isocytosine," *Biochemistry*, 2000, vol. 39, pp. 10177-10188.
International Search Report dated Jun. 16, 2006.
Beaucage, Serge et al., "Deoxynucleotide phosphoramidites—a new class of key intermediates for deoxypolynucleotide synthesis," *Tetrahedron Letters*, 1981, vol. 22(20), pp. 1859-1862.
Supplemental European Search Report dated May 26, 2008 for EP 05760503.2.
Examination Report issued in European Appln. No. 05760503.2 dated Nov. 6, 2009.

* cited by examiner

*Primary Examiner*—Patrick T Lewis
(74) *Attorney, Agent, or Firm*—Foley & Lardner LLP

(57) ABSTRACT

The present invention provides the combination of the O-2 diphenylcarbamoyl ("DPC") and N-6 dimethylaminomethylidene ("DMF") protecting groups for isoguanosine nucleosides that can be utilized in oligonucleotide synthesis.

12 Claims, No Drawings

REAGENTS FOR THE IMPROVED SYNTHESIS OF ISOGUANOSINE CONTAINING OLIGONUCLEOTIDES

FIELD OF THE INVENTION

This invention relates generally to compounds for oligonucleotide synthesis. In particular, the present invention relates to improved protecting groups for isoguanosine nucleosides.

BACKGROUND OF THE INVENTION

Oligonucleotides are essential reagents in many important molecular biology experiments, assays and information gathering operations, such as the polymerase chain reaction (PCR), diagnostic probes, single nucleotide polymorphism (SNP) detection, and genomic sequencing. The benefits of conducting the synthesis of oligonucleotides by the sequential addition and covalent attachment of monomeric units onto a solid support is well appreciated. In particular, the method of Caruthers is highly optimized and almost universally adopted (U.S. Pat. Nos. 4,458,066 and 4,973,679). The vast majority of the millions of oligonucleotides consumed each year are prepared by automated synthesis with phosphoramidite nucleoside monomers (Beaucage (1992) Tetrahedron Lett. 22:1859-62; U.S. Pat. No. 4,415,732).

The key step in oligonucleotide synthesis is the specific and sequential formation of internucleotide phosphate linkages between a 5'-OH group of one nucleotide and a 3'-OH group of another nucleotide. Accordingly, in the typical synthesis of oligonucleotides, the phosphate group of an "incoming" nucleotide is combined with the 5'-OH group of another nucleotide (i.e. the 5'-OH group is "phosphorylated" or "phosphitylated"). These groups must be capable of actively participating in the synthesis of the oligonucleotide. Thus, the 5'-OH groups are modified (typically with a dimethoxy trityl ("DMT") group) such that an investigator can introduce two such nucleotides into a reaction chamber and adjust the conditions therein so that the two nucleotides are properly combined; by a series of successive such additions, a growing oligonucleotide having a defined sequence can be accurately generated.

The four bases of the nucleosides, adenine, thymine (uracil in the case of RNA), guanosine and cytosine, include moieties which are chemically reactive (e.g., exocyclic amino groups). These groups, unlike the 3'-OH and 5'-OH groups, must be "temporarily" protected, i.e. the protecting groups must be capable of blocking any reactive sites on the base until after the oligonucleotide synthesis is completed; after such synthesis is completed, these groups must also be capable of being removed from the bases such that the biological activity of the oligonucleotide is not affected.

The principal reason for temporarily protecting the base is that in the absence of such protecting groups, the exocyclic amino groups ("NH$_2$") of the bases can compete for binding to the 5'-OH group. If such a reaction takes place, the resulting product will not be useful. Accordingly, these protecting groups are important in reducing the occurrence of "side product formation" i.e. the formation of chemically similar, but unwanted, materials. To date, the most widely used protecting groups used in conjunction with the phosphoramidite methodologies for oligonucleotide synthesis are benzoyl for A and C, and isobutyryl for G and C, (thymine, which does not have an amino group, does not ordinarily require a protecting group).

Despite the structural similarities that iso-G shares with the standard bases, it has not been trivial to convert procedures and protecting groups used for the automated solid-phase synthesis of standard oligonucleotides to be suitable for preparing oligonucleotides containing iso-G. Accordingly, the synthesis of oligonucleotides and their analogs that employ the widely used protecting groups remains a tedious and costly process. There remains an ongoing need in this area for developing improved synthetic processes that facilitate the synthesis of oligonucleotides.

SUMMARY

The invention pertains to the use of improved protecting groups for the successful incorporation of an isoguanosine ("iso-G") nucleotide into a synthetic oligonucleotide (see Formula 1).

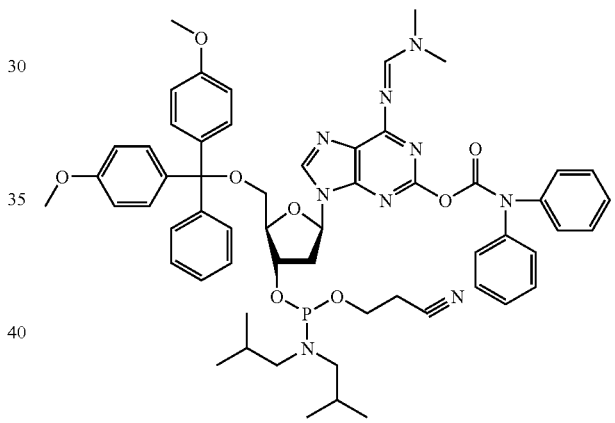

Formula 1

A surprising and unexpected aspect of the invention is that the combination of the O-2 diphenylcarbamoyl ("DPC") and N-6 dimethylaminomethylidene ("DMF") protecting groups provides an isoguanosine phosphoramidite that can be utilized in oligonucleotide synthesis by the phosphoramidite method using the reaction protocols used for the standard, natural A,G,T, and C phosphoramidite reagents. This is an improvement over previously known isoguanosine phosphoramidites that required extended coupling times, higher concentrations, or special post-synthetic treatment compared to the A,G,T, and C phosphoramidite reagents. The improvement of the isoguanosine phosphoramidite reagent, however, is not limited to this exact composition of protecting groups. Further improvement to the reagent either in its synthesis or performance in oligonucleotide synthesis maybe possible with the modification of the specific protecting group—for example, it is anticipated that DPC analogs, in combination with the DMF protecting group, may further enhance oligonucleotide synthesis (see Formula 2).

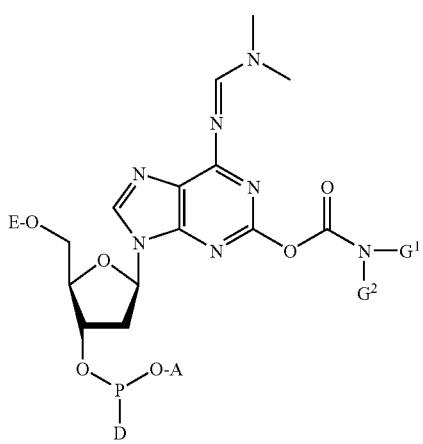

Formula 2

The use of the N-6 dimethylaminomethylidene (DMF) protecting group on iso-G phosphoramidites is an improvement over the larger formamidine protecting groups such as the widely used diisobutyl formamidine described in the literature for four reasons. First, due to the decreased hydrophobicity of the DMF group, the iso-G nucleoside remains unusually polar over the course of the process of phosphoramidite synthesis thus allowing for the clean precipitation of nucleoside intermediates at each step of the synthesis process. Until now, an extra column purification process had to be performed after each step to ensure the purity of the final phosphoramidite. Column purification is undesirable because it adds a significant labor cost to the process and also limits the scale of synthesis that can be executed easily. Second, due to the decreased size of the DMF group, the efficiency of the phosphoramidite in oligonucleotide synthesis is increased. The increase in efficiency is significant enough that the DMF-protected iso-G phosphoramidite can be used in oligonucleotide synthesis in the same manner as a standard phosphoramidite. Until now, longer coupling times, double couplings and higher phosphoramidite concentrations had to be employed to dependably synthesize iso-G containing oligonucleotides. Third, and also because of the smaller size of the DMF group, the deprotection times of oligonucleotides synthesized with DMF-protected phosphoramidites is decreased significantly. Until now, deprotection times had to be significantly lengthened whenever an oligo containing an iso-G had been synthesized. This is undesirable because obviously it takes longer to complete the synthesis process, but also the longer exposure times to alkaline conditions necessary to remove the iso-G protecting group causes damage to sensitive dye molecules that are sometimes present as well as general oligonucleotide decomposition. Fourth, the DMF protection is easier to introduce synthetically into the phosphoramidite structure because the reagent used is readily commercially available. The other formamidine reagents on the other hand require an extra synthetic step before the formamidine group can be added to the structure.

DETAILED DESCRIPTION

Although Formula 1 illustrates the preferred embodiment of the present invention, the invention is not limited thereto. Those skilled in the art will appreciate that various functional groups may be substituted for others, wherein the resulting composition will still achieve the desired properties as described herein.

Aliphatic groups, as used herein, include straight chained or branched $C_1$-$C_{18}$ hydrocarbons which are completely saturated or which contain one or more non-aromatic double bonds, or cyclic $C_3$-$C_{18}$ hydrocarbons which are completely saturated or which contain one or more unconjugated double bonds. Lower alkyl groups are straight chained or branched $C_1$-$C_8$ hydrocarbons or $C_3$-$C_8$ cyclic hydrocarbons which are completely saturated. Aliphatic groups are preferably lower alkyl groups.

Aromatic groups include carbocyclic aromatic ring systems (e.g., phenyl) and carbocyclic aromatic ring systems fused to one or more carbocyclic aromatic or non-aromatic ring (e.g., naphthyl, anthracenyl and 1,2,3,4-tetrahydronaphthyl).

Heteroaromatic groups, as used herein, include heteroaryl ring systems (e.g., thienyl, pyridyl, pyrazole, isoxazolyl, thiadiazolyl, oxadiazolyl, indazolyl, furans, pyrroles, imidazoles, pyrazoles, triazoles, pyrimidines, pyrazines, thiazoles, isoxazoles, isothiazoles, tetrazoles, or oxadiazoles) and heteroaryl ring systems in which a carbocyclic aromatic ring, carbocyclic non-aromatic ring, heteroaryl ring or a heterocycloalkyl ring is fused to one or more other heteroaryl rings (e.g., benzo(b)thienyl, benzimidazole, indole, tetrahydroindole, azaindole, indazole, quinoline, imidazopyridine, purine, pyrrolo[2,3-d]pyrimidine, and pyrazolo[3,4-d]pyrimidine).

An aralkyl group, as used herein, is an aromatic substituent that is linked to a moiety by an aliphatic group preferably having from one to about six carbon atoms. A heterocycloalkyl group, as used herein, is a non-aromatic ring system that preferably has 5 to 6 atoms and includes at least one heteroatom, such as nitrogen, oxygen, or sulfur. Examples of heterocycloalkyl groups include morpholines, piperidines, and piperazines.

Suitable substituents for aliphatic groups, aromatic groups, aralkyl groups, heteroaromatic groups and heterocycloalkyl groups include aromatic groups, halogenated aromatic groups, lower alkyl groups, halogenated lower alkyl (e.g. trifluoromethyl and trichloromethyl), —O-(aliphatic group or substituted aliphatic group), —O-(aromatic group or substituted aromatic group), benzyl, substituted benzyl, halogens, cyano, nitro, —S-(aliphatic or substituted aliphatic group), and —S-(aromatic or substituted aromatic).

As used herein, a "protecting group" is a chemical group that is attached to a functional moiety (for example to the oxygen in a hydroxyl group or the nitrogen in an amino group, replacing the hydrogen) to protect the functional group from reacting in an undesired way. It is obviously desirable that a protecting group be "orthogonal;" i.e., removable with reagents that do not affect all of the protecting groups of the molecule. Protecting group terminology follows the general strategies taught by Greene, T. and Wuts, P. "Protective Groups in Organic Synthesis", Third Edition, John Wiley & Sons, Inc., New York, N.Y. (1999) and suitable protecting groups are known to one ordinarily skilled in the art.

In compounds of Formula 2, A is an O-phosphoramidite protecting group orthogonal to E where A may be removed through an elimination process as disclosed in U.S. Pat. No. 4,725,677, which is incorporated herein by reference. Each A is, independently, cyanoethyl (—$CH_2CH_2CN$), a substituted or unsubstituted aliphatic group, or a substituted or unsubstituted aromatic group. Preferably, the A group is cyanoethyl.

When the phosphoramidite is employed, D is a disubstituted nitrogen having the formula —$NT^1T^2$, where $T^1$ and $T^2$ are each, independently, a substituted or unsubstituted aliphatic group, a substituted or unsubstituted aromatic group, a substituted or unsubstituted aralkyl group; or T1 and T2 taken together with the nitrogen to which they are bonded form a heterocycloalkyl group or a heteroaromatic group, in which the heterocycloalkyl group or heteroaromatic ring is preferably a five or six membered ring. Preferably, each T1 and T2 is an isopropyl group.

$G^1$ and $G^2$ are substituted or unsubstituted hydrocarbon radicals that may be the same or different and may have from 0 to 5 heteroatoms, primarily oxygen, sulfur, nitrogen, or halogen. The two G's may be taken together to form a mono- or poly-, homo- or heterocycle having a total of 1 to 3 annular members. Usually, the two G's will have a total of from 1 to 20, more usually 2 to 12 carbon atoms, where the G's may be aliphatic or aromatic monovalent, or, when taken together, divalent radicals, or substituted or unsubstituted, homo- or heterocycles. Preferably, $G^1$ and $G^2$ will each be a phenyl group.

In Formula 2, E is a protecting group, preferably an acid labile protecting group or a tri-substituted silyl group such as t-butyldimethylsilyl, triisopropylsilyl, or t-butyldiphenylsilyl. In a more preferred embodiment, E is a substituted or unsubstituted trityl or 9-(phenyl-) xanthenyl (hereinafter "pixyl"). In an even more preferred embodiment, E is a substituted trityl or pixyl. Most preferably, E is 4,4'-dimethoxytrityl.

An acid labile protecting group is a protecting group which can be removed by contacting the group with a Bronsted or a Lewis acid. Acid labile protecting groups are known to those skilled in the art. Examples of common acid labile protecting groups include substituted or unsubstituted trityl groups (Greene, et al., Protective Groups in Organic Synthesis (1991), John Wiley & Sons, Inc., pages 60-62, the teachings of which are incorporated herein by reference in their entirety), substituted or unsubstituted tetrahydropyranyl groups (Id., pages 31-34), substituted or unsubstituted tetrahydrofuranyl groups (Id., pages 36-37) or pixyl groups (Id., page 65). A preferred acid labile protecting group is a substituted or unsubstituted trityl, for example 4,4'-dimethoxytrityl (hereinafter "DMT"). Trityl groups are preferably substituted by electron donating substituents such as alkoxy groups.

In some situations it may be desirable to substitute for E with a different group after completion of the synthesis of the oligomer. Depending upon the blocking group, particularly where a trityl group is employed, and the nature of the enzyme employed to degrade the incomplete oligomers, the hydrolytic conditions may result in a significant proportion of the E groups being removed. Under these conditions, complete oligomers may also be degraded resulting in substantial diminution of the yield of the oligomer.

In order to avoid degradation of complete oligomers by an exonuclease, the E group may be replaced with a different blocking group, which is stable under the conditions of the exonucleolytic conditions. Such a group will be characterized by being retained during the removal of the capping group, being retained during the exonucleolytic conditions, and being removable without degradation of the oligomer, either by itself or in conjunction with cleavage from the support.

Rather than remove the blocking group and substitute an alternative group, depending upon the substitute blocking group, e.g., carboxylic acid ester, phosphate, etc., the ultimate nucleotide may be prepared with the substitute blocking group present. Thus, by having prepared nucleotides containing the substituted blocking group, these may be added in the last step where the manual or automated procedure permits using a different nucleotide.

The invention also concerns a process for the production of oligonucleotides consisting of 6 to 100 nucleotide building blocks according to the oligonucleotide synthesis process in which, depending on the sequence design, appropriate 2'-deoxy-isoguanosines or isoguanosines according to the invention are used wherein a starting nucleoside is bound to a solid support and subsequently the desired oligonucleotide is assembled by stepwise coupling using appropriately activated monomeric nucleotide building blocks, if desired trivalent phosphorus is oxidized to pentavalent phosphorus during or after the synthesis, the oligonucleotide is cleaved from the support with a first base, heterocyclic protecting groups are cleaved with a second base, the 5' protecting group is cleaved with an acid and the oligonucleotide is purified if desired. The purification is preferably carried out by reverse phase or anion exchange HPLC. This is usually followed by a desalting, for example by dialysis. The production of the monomeric nucleotide building blocks is carried out according to the methods familiar to a person skilled in the art such as those disclosed by Gait, M. J. in "Oligonucleotide Synthesis, A Practical Approach," IRL Press, Ltd. (1984).

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, an group having 1-3 atoms refers to groups having 1, 2, or 3 atoms. Similarly, a group having 1-5 atoms refers to groups having 1, 2, 3, 4, or 5 atoms, and so forth.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present invention, thus generally described, will be understood more readily by reference to the following examples, which are provided by way of illustration and are not intended to be limiting of the present invention.

Method of Synthesis $N^6$-[(Dimethylamino)methylidene]-2'-deoxy-isoguanosine

2'-deoxy-isoguanosine (5 g, 18.7 mmol) is dissolved in methanol (70 mL), dimethylformamide dimethylacetal (22.5 mmol, 3 mL, 1.2 eq.) is added and the mixture is stirred at ambient temperature for 2 h. The solvents are removed by rotary evaporation under reduced pressure. The material is used in the next step without further purification.

$N^6$-[(Dimethylamino)methylidene]-$O^2$-(diphenylcarbamoyl)-2'-deoxy-isoguanosine $N^6$-[(Dimethylamino)methylidene]-2'-deoxy-isoguanosine obtained above is dissolved in pyridine (192 mL) and diphenylcarbamyl chloride (22.5 mmol, 5.2 g, 1.0 eq) is added with stirring. The mixture is stirred 5 h at ambient temperature before it is dried by rotary evaporation under reduced pressure. The resulting residue is twice redissolved in toluene and dried by rotary evaporation. The product is purified by silica gel chromatography using a mixture of methanol/chloroform (6:94). Yield 40%.

5'-O-(4,4'-Dimethoxytrityl)-N⁶-[(dimethylamino)methylidene]-O²-(diphenylcarbamoyl)-2'-deoxy-isoguanosine N⁶-[(Dimethylamino)methylidene]-O²-(diphenylcarbamoyl)-2'-deoxy-isoguanosine obtained above is dissolved in pyridine (27 mL) and 4,4'-dimethoxytritylchloride (9 mmol, 3.05 g, 1.1 eq.) is added with stirring. The mixture is stirred 5 h at ambient temperature before methanol (2 mL) is added and the solvents removed by rotary evaporation under reduced pressure. The residue is taken up in ethyl acetate and extracted with 5% NaHCO₃ twice. The ethyl acetate solution is dried with Na₂SO₄ before the solvent is removed by rotary evaporation under reduced pressure. The product is purified from the resulting oil by silica gel chromatography using a mixture of methanol/chloroform (4:96). Yield 40%.

5'-O-(4,4'-Dimethoxytrityl)-N⁶-[(dimethylamino)methylidene]-O²-(diphenylcarbamoyl)-2'-deoxy-isoguanosine-3'-O-(2-cyanoethyl-N,N'-diisopropylphosphoramidite)

5'-O-(4,4'-Dimethoxytrityl)-N⁶-[(dimethylamino)methylidene]-O²-(diphenylcarbamoyl)-2'-deoxy-isoguanosine is dissolved in methylene chloride (50 mL) before diisopropylethylamine (15.8 mmol, 2.7 mL, 4.4 eq.) and 2-cyanoethyl diisopropyl-phosphoramidochloridite (5.0 mmol, 1.15 mL, 1.4 eq.) are added with stirring. The mixture is stirred at ambient temperature 1 h before the solvent is removed by rotary evaporation under reduced pressure. The product is purified from the resulting foam by silica gel chromatography using a mixture of hexanes/chloroform/ethyl acetate/triethylamine (40:35:35:2). The purified product is redissolved in a minimal volume of ethyl acetate and then precipitated by addition of hexane. Yield 76%.

While preferred embodiments have been illustrated and described, it should be understood that changes and modifications can be made therein in accordance with ordinary skill in the art without departing from the invention in its broader aspects as defined in the following claims.

What is claimed is:

1. A compound of the formula:

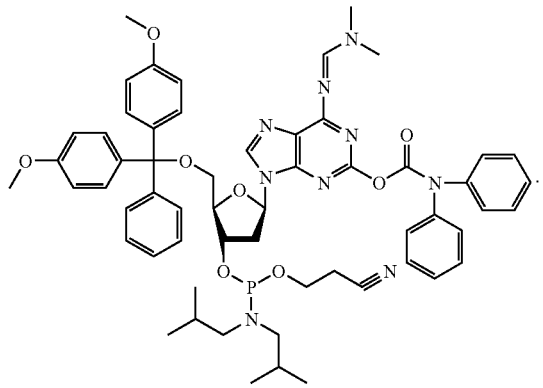

2. A compound of the formula:

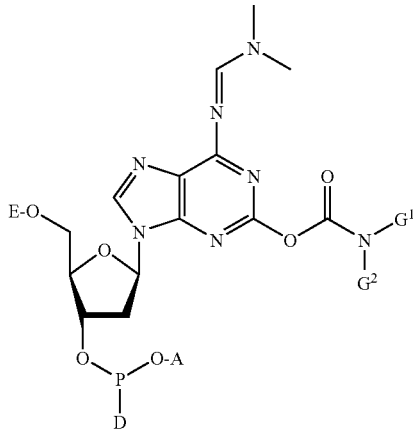

wherein
E is an acid labile protecting group;
A is an O-phosphoramidite protecting group orthogonal to E;
D is NT¹T² wherein
T¹ and T² are each, independently, a substituted or unsubstituted aliphatic group, a substituted or unsubstituted aromatic group, a substituted or unsubstituted aralkyl group; or
T¹ and T² taken together with the nitrogen to which they are bonded form a heterocycloalkyl group or a herteroaromatic group; and
G¹ and G² are substituted or unsubstituted hydrocarbon radicals.

3. The compound of claim 2 wherein E is a substituted trityl or pixyl.

4. The compound of claim 2 wherein A is, independently, cyanoethyl, a substituted or unsubstituted aliphatic group, or a substituted or unsubstituted aromatic group.

5. The compound of claim 2 wherein G¹ and G² are each a phenyl group.

6. The compound of claim 2 wherein E is 4',4-dimethoxytrityl.

7. The compound of claim 2 wherein A is cyanoethyl.

8. The compound of claim 2 wherein T¹ and T² is an isopropyl group.

9. The compound of claim 2 wherein T¹ and T² are each independently a substituted or unsubstituted aliphatic group.

10. The compound of claim 9 wherein T¹ and T² are each independently a lower alkyl group.

11. The compound of claim 2 wherein G¹ and G² are each independently a substituted or unsubstituted aliphatic or aromatic monovalent, or, when taken together, divalent radical, having from one to 20 carbon atoms.

12. The compound of claim 11 wherein G¹ and G² are each a substituted or unsubstituted aromatic group.

* * * * *